United States Patent
Mochizuki et al.

(10) Patent No.: US 9,415,164 B2
(45) Date of Patent: Aug. 16, 2016

(54) MEDICAL PUMP SYSTEM AND MEDICAL PUMP MOUNTING RACK

(71) Applicant: TERUMO KABUSHIKI KAISHA, Shibuya-ku (JP)

(72) Inventors: Tomonori Mochizuki, Ashigarakami-gun (JP); Tomoko Uemura, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 570 days.

(21) Appl. No.: 13/960,528

(22) Filed: Aug. 6, 2013

(65) Prior Publication Data

US 2013/0324929 A1     Dec. 5, 2013

Related U.S. Application Data

(63) Continuation of application No. PCT/JP2012/000678, filed on Feb. 1, 2012.

(30) Foreign Application Priority Data

Feb. 8, 2011    (JP) .................................. 2011-025318

(51) Int. Cl.
    *A61M 5/172*       (2006.01)
    *A61M 5/142*       (2006.01)
    (Continued)

(52) U.S. Cl.
    CPC .............. *A61M 5/1723* (2013.01); *A61M 5/142* (2013.01); *A61M 5/168* (2013.01);
    (Continued)

(58) Field of Classification Search
    CPC .................. A61M 2205/35; A61M 2205/3569; A61M 2205/3576; A61M 2205/502; A61M 5/142; A61M 5/168; A61M 5/1723; A61M 5/1413; A61M 5/1415; G06F 19/3406; G06F 19/3412; G06F 19/3468
    See application file for complete search history.

(56) References Cited

U.S. PATENT DOCUMENTS 5,788,688 A * 8/1998 Bauer .................... A61B 90/36
                                                                606/1
5,867,372 A * 2/1999 Shie ........................ H05K 7/186
                                                                174/564

(Continued)

FOREIGN PATENT DOCUMENTS

| CN | 1946085 A | 4/2007 |
|----|-----------|--------|
| EP | 1 157 711 A2 | 11/2001 |

(Continued)

OTHER PUBLICATIONS

Office Action issued on Apr. 20, 2015, by the Japanese Patent Office in corresponding Japanese Patent Application No. 2011-025318. (3 pages).

(Continued)

*Primary Examiner* — Quynh-Nhu H Vu
(74) *Attorney, Agent, or Firm* — Buchanan Ingersoll & Rooney PC

(57) ABSTRACT

A medical pump system includes a plurality of medical pumps mounted in a rack, the rack determines whether it has received a start notification indicating the start of setting operation or an end notification indicating the end of setting operation from one of the mounted medical pumps via a communication unit for communicating with the mounted medical pumps. Upon receiving a start notification from one medical pump, the rack transmits an inhibition instruction to inhibit the acceptance of user operation to all remaining medical pumps via the communication unit. Upon receiving an end notification from one medical pump, the rack transmits a cancellation instruction to cancel the inhibition state based on the inhibition instruction to all the remaining medical pumps. Each of the medical pumps mounted in the rack inhibits the acceptance of user operation in an interval between reception of start instruction and reception of a cancellation instruction.

7 Claims, 9 Drawing Sheets

(51) Int. Cl.
*A61M 5/168* (2006.01)
*G06F 19/00* (2011.01)

(52) U.S. Cl.
CPC ....... *G06F 19/3406* (2013.01); *G06F 19/3412* (2013.01); *G06F 19/3468* (2013.01); *A61M 2205/35* (2013.01); *A61M 2205/3569* (2013.01); *A61M 2205/3576* (2013.01); *A61M 2205/502* (2013.01)

(56) References Cited

U.S. PATENT DOCUMENTS

| | | | |
|---|---|---|---|
| 6,544,228 | B1 | 4/2003 | Heitmeier |
| 2002/0134570 | A1* | 9/2002 | Franklin-Lees ..... A61M 5/1413 174/58 |
| 2005/0085760 | A1 | 4/2005 | Ware et al. |
| 2006/0206356 | A1* | 9/2006 | Vanderveen ........ A61M 5/1407 705/2 |
| 2007/0080223 | A1 | 4/2007 | Japuntich |
| 2007/0201992 | A1* | 8/2007 | Mernoe ............. A61M 5/14216 417/321 |
| 2007/0219495 | A1 | 9/2007 | Kato et al. |
| 2009/0177188 | A1 | 7/2009 | Steinkogler |

FOREIGN PATENT DOCUMENTS

| | | |
|---|---|---|
| JP | 11-347118 A | 12/1999 |
| JP | 2003-070910 A | 3/2003 |
| JP | 2003-513761 A | 4/2003 |
| JP | 2006-171092 A | 6/2006 |
| JP | 2007-519431 A | 7/2007 |
| JP | 2007-252405 A | 10/2007 |
| JP | 2008-167888 A | 7/2008 |
| JP | 2008-532635 A | 8/2008 |
| JP | 2008-540004 A | 11/2008 |
| JP | 2010-217223 A | 9/2010 |
| JP | 2012-070992 A | 4/2012 |
| WO | 01/36027 A1 | 5/2001 |
| WO | 2005/050523 A2 | 6/2005 |

OTHER PUBLICATIONS

International Search Report (PCT/ISA/210) issued on Mar. 19, 2012, by the Japanese Patent Office as the International Searching Authority for International Application No. PCT/JP2012/000678.
Written Opinion (PCT/ISA/237) issued on Mar. 19, 2012, by the Japanese Patent Office as the International Searching Authority for International Application No. PCT/JP2012/000678.
Office Action issued on Sep. 30, 2014, by the Chinese Patent Office in corresponding Chinese Patent Application No. 2012800008074.9 (5 pgs).

* cited by examiner

MEDICAL PUMP SYSTEM AND MEDICAL PUMP MOUNTING RACK

This application is a continuation of International Application No. PCT/JP2012/000678 filed on Feb. 1, 2012, and claims priority to Japanese Application No. 2011-025318 filed on Feb. 8, 2011, the entire content of both of which is incorporated herein by reference.

BACKGROUND OF THE INVENTION

1. Field of the Invention

The present invention relates to a medical pump system including a plurality of medical pumps mounted in a rack and a medical pump mounting rack.

2. Description of the Related Art

In a hospital or the like, in order to infuse a drug or the like into the body of a patient, there is used an infusion pump which injects a liquid in an infusion bag into the patient through an infusion tube at a controlled infusion speed or a syringe pump which injects the content of a syringe into the patient at a controlled infusion speed. In general, such an infusion pump or a syringe pump (these pumps will be collectively termed medical pumps in this specification) is required as one medical pump to infuse one type of drug. For this reason, in order to simultaneously administer a plurality of types of drugs into a patient in an operating room, intensive care unit, or the like, it is necessary to use a plurality of medical pumps corresponding to the types of drugs. In such a case, juxtaposing a plurality of medical pumps on a desk or placing them on a floor will take space. In addition, it is not easy to move these pumps. The common practice is therefore to use a rack for arranging and mounting medical pumps.

When a plurality of medical pumps are mounted in a rack, it is cumbersome to make various types of settings by individually operating each medical pump and monitor each medical pump. Under the circumstances, PTL 1 discloses an arrangement configured to provide a central control unit which communicates with each medical pump mounted in a rack so as to allow the central control unit to monitor the connection form and infusion state of each medical pump.

CITATION LIST

Patent Literature

PTL 1: Japanese Patent Laid-Open No. 11-347118

SUMMARY OF THE INVENTION

When wanting to individually change settings for medical pumps in accordance with the condition of a patient, the user changes settings for a medical pump requiring setting changes by directly operating the pump. This operation is the same as when using the central control unit as in PLT 1. In a medical site, while performing a series of setting operations for one medical pump, the user sometimes must temporarily interrupt the setting operation to check the state of another medical pump or perform another operation. Since a plurality of similar medical pumps are mounted in the rack, when the user tries to resume setting operation after such interruption, he/she may mistakenly operate a wrong medical pump. Recently, in particular, the mounting density of medical pumps in a rack has increased, an operation error like that described above has been more likely to occur.

The present invention has been made in consideration of the above problem, and has as its object to prevent the user from mistakenly operating a wrong medical pump while operating a given medical pump when a plurality of medical pumps are mounted in a rack.

A medical pump system according to an aspect of the present invention which is configured to achieve the above object has the following arrangement. That is, there is provided a medical pump system including a plurality of medical pumps mounted in a rack, wherein the rack comprises a communication unit configure to communicate with a plurality of mounted medical pumps, a determination unit configured to determine whether a start notification indicating a start of setting operation or an end notification indicating an end of setting operation is received from one of the plurality of medical pumps via the communication unit, a first transmission unit configured to, if the determination unit determines that the start notification is received from the one medical pump, transmit an inhibition instruction to inhibit acceptance of user operation to all remaining medical pumps except for the one medical pump via the communication unit, and a second transmission unit configured to, if the determination unit determines that the end notification is received from the one medical pump, transmit a cancellation instruction to cancel the inhibition state set by the inhibition instruction to all the remaining medical pumps, and each of the plurality of medical pumps comprises a control unit configured to inhibit acceptance of user operation during an interval between reception of the inhibition instruction and reception of the cancellation instruction.

Advantageous Effects of Invention

According to the present invention, it is possible to prevent the user from mistakenly operating a wrong medical pump while operating a given medical pump when a plurality of medical pumps are mounted in a rack.

Other features and advantages of the present invention will be apparent from the following description taken in conjunction with the accompanying drawings. Note that the same reference numerals denote the same or like components throughout the accompanying drawings.

BRIEF DESCRIPTION OF THE DRAWINGS

The accompanying drawings, which are incorporated in and constitute a part of the specification, illustrate exemplary embodiments of the invention and, together with the description, serve to explain the principles of the present invention.

DESCRIPTION OF THE EMBODIMENTS

The preferred embodiments of the present invention will be described below with reference to the accompanying drawings.

First Embodiment

Figure 1:
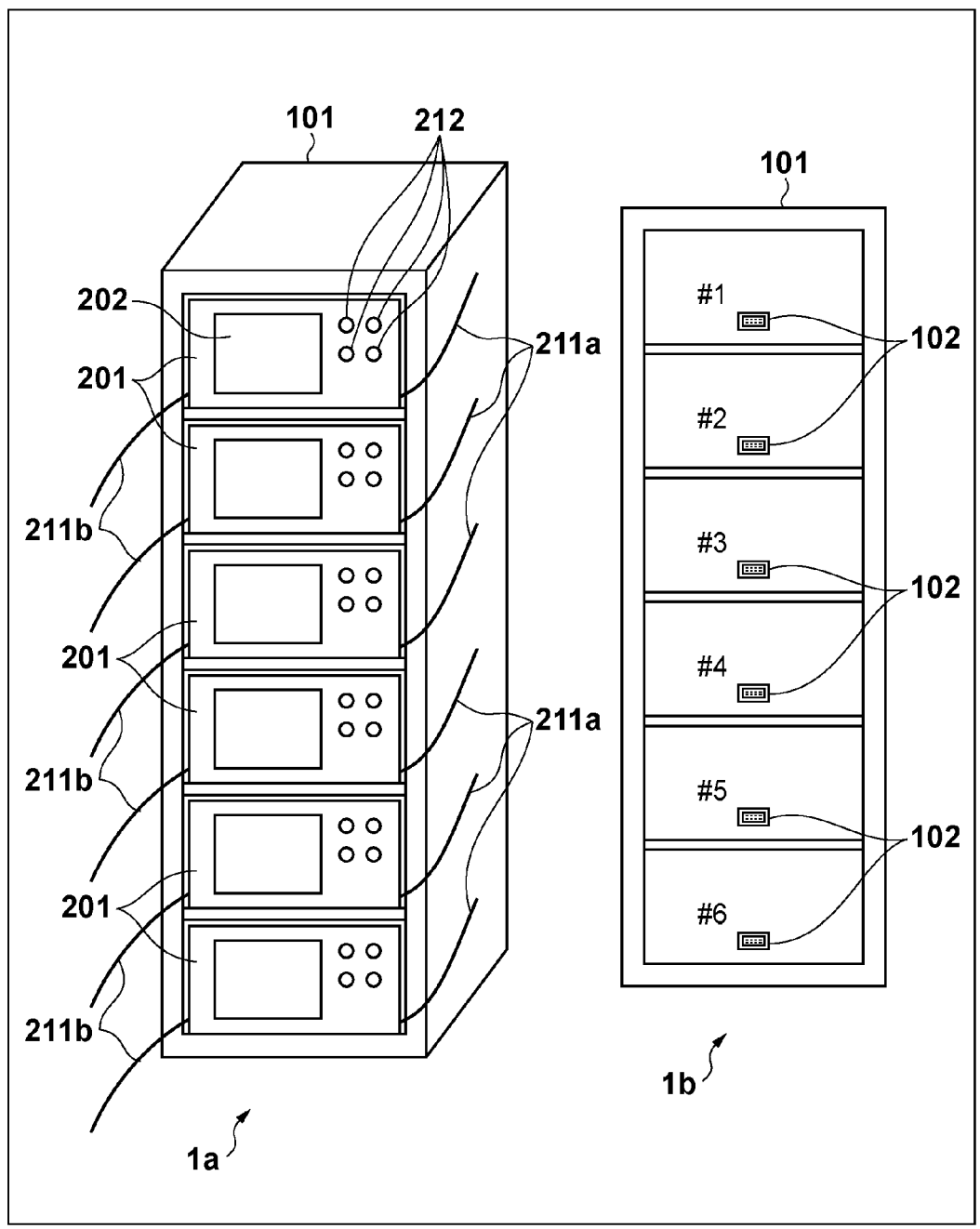
FIG. 1 is a view for explaining an example of the overall arrangement of a medical pump system and a medical pump mounting rack.

In FIG. 1, 1a shows an example of the external arrangement of a medical pump system according to the first embodiment. As indicated by the external arrangement 1a in FIG. 1, this embodiment will exemplify the medical pump system configured to mount a plurality of medical pumps (six pumps in this example) in a dedicated rack. In the external arrangement 1a, reference numeral 101 denotes a medical pump mounting rack (to be referred to as the rack 101). In this case, this rack is configured to allow up to six medical pumps 201 to be mounted in a line in the vertical direction. The arrangement shown in FIG. 1 uses an infusion pump as an example of the medical pump 201. A tube 211 for infusing a drug is mounted in each pump. Note however that the number of medical pumps mounted is not limited to this, and that the medical pumps to be used are not limited to infusion pumps, and various types of medical pumps such as syringe pumps can be mounted. Reference numeral 212 denotes an operation unit including switches for making various types of settings such as flow rate settings in the medical pumps 201.

In FIG. 1, 1b shows the eternal arrangement of the rack 101, viewed from the front, with no medical pumps 201 being mounted. The rack 101 has a plurality of (six in this case) ports 102 arranged in correspondence with the mount positions of a plurality of pumps. Each of the plurality of ports 102 is formed from a connector which can be connected to the corresponding medical pump 201. Each medical pump 201 communicates with the rack 101 via the corresponding port 102. Note that the ports 102 are respectively assigned with numbers #1, #2, ..., #6, beginning at the top, in the order of the mount positions of the vertically arranged pumps.

Figure 2:
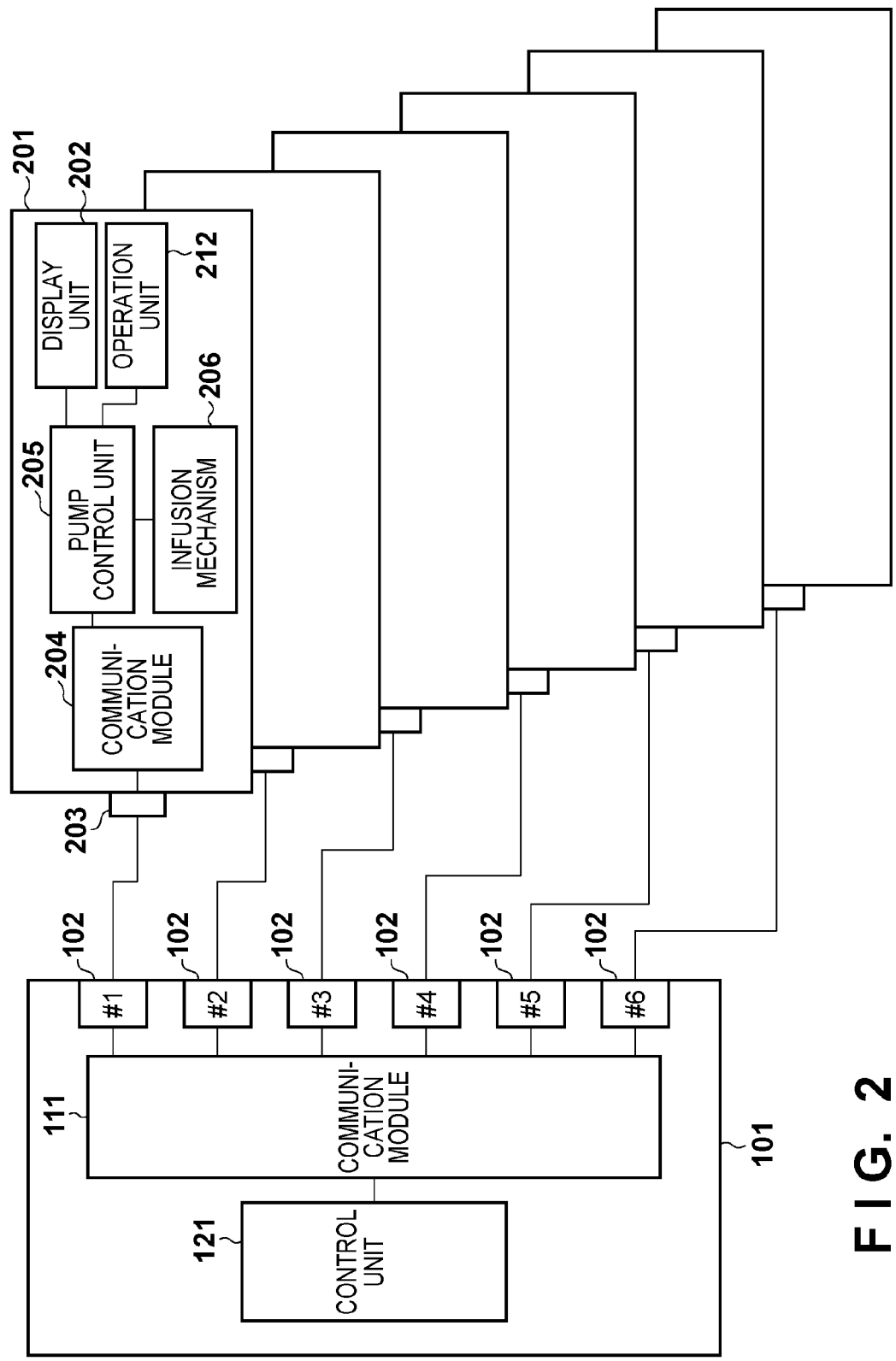
FIG. 2 is a block diagram showing a control arrangement for the medical pump mounting rack and medical pumps according to the first embodiment.

FIG. 2 is a block diagram showing an example of a control arrangement for the rack 101 and the medical pumps 201 according to the first embodiment. The six ports 102 of the rack 101 each are connected to a communication module 111. Upon receiving a signal (data) from the medical pump 201 via the port 102, the communication module 111 notifies a control unit 121 of the received data and the number of the port (one of the port numbers #1 to #6) from which the data is received. Upon receiving a pair of a port number and data (command or the like) from the control unit 121, the communication module 111 outputs the data received from the control unit 121 to the port 102 corresponding to the received port number. In this manner, the control units 121 of the rack 101 can individually communicate with the plurality of mounted medical pumps 201, respectively. Note that each control unit 121 includes a CPU (not shown) such as a microcomputer, a ROM (not shown) storing control programs for the overall apparatus which are executed by the CPU and various types of data, and a RAM (not shown) serving as a work area and temporarily storing measured data and various types of data. The control unit 121 executes various types of processing including determination (decision) and processing shown in the flowchart of FIG. 4.

In each medical pump 201, a display unit 202 includes, for example, a liquid crystal panel. The display unit 202 executes various types of display operations under the control of a pump control unit 205 which comprises a CPU (not shown) such as a microcomputer, a ROM (not shown) storing control programs for the overall apparatus which are executed by the CPU and various types of data, and a RAM (not shown) serving as a work area and temporarily storing measured data and various types of data, and executes various types of determination (decision) and processing. Connectors 203 are connected to the ports 102 to implement electrical connection (communication) to the medical pumps 201. Assume that the connectors 203 are connected to the ports 102 via cables. Alternatively, the connectors 203 may be directly connected to the ports 102 (for example, the connectors 203 may be connected to the ports 102 by mounting the medical pumps 201 in the rack 101). Each pump control unit 205 controls a corresponding infusion mechanism 206 to control the infusion amount. If the medical pump 201 is an infusion pump, the infusion mechanism 206 includes a plurality of fingers for infusion. The plurality of fingers sequentially press the infusion tube to discharge a drug in the tube. If the medical pumps 201 is a syringe pump, the infusion mechanism 206 is provided with a syringe to be configured to press its plunger. The operation unit 212 accepts various types of setting operations by the user, for example, flow rate setting operation.

In each medical pump 201 having the above arrangement, upon accepting an operation input from the user via the operation unit 212, the pump control unit 205 transmits a notification indicating the start of operation (to be referred to as a start notification) to the rack 101 via a communication module 204 and the connector 203. Upon detecting the end of a series of operations via the operation unit 212, the pump control unit 205 transmits a notification indicating the end of operation (to be referred to as an end notification) to the rack 101 via the communication module 204 and the connector 203. Upon receiving an inhibition instruction from the rack 101 via the connector 203 and the communication module 204, the pump control unit 205 inhibits accepting user operation from the operation unit 212 and decreases the display luminance of the display unit 202. In addition, upon receiving a cancellation instruction from the rack 101 via the connector 203 and the communication module 204, the pump control unit 205 cancels the above inhibition state based on the inhibition instruction. That is, the pump control unit 205 resumes (permits) accepting user operation from the operation unit 212, and restores the display luminance of the display unit 202. This operation will be described with reference to the flowchart of FIG. 3.

Figure 3:
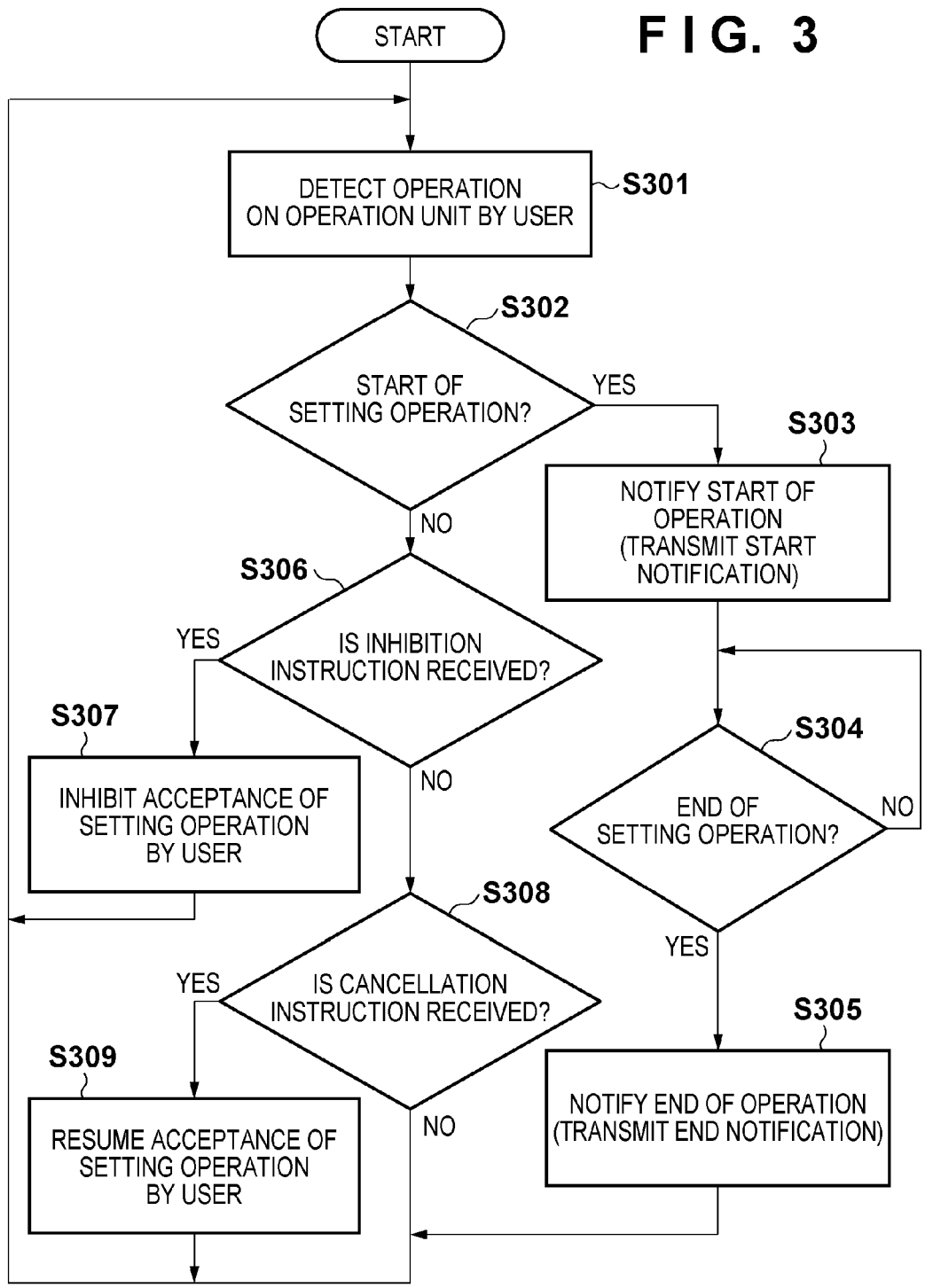
FIG. 3 is a flowchart showing a control procedure for the medical pumps according to the first embodiment.

FIG. 3 is a flowchart for explaining the operation of each medical pumps 201. In step S301, the pump control unit 205 detects user operation on the operation unit 212. In step S302, the pump control unit 205 determines whether the start of setting operation for a flow rate setting and the like. The start of setting operation may include, for example, the selection of a setting item and the input of a set value after the selection of a setting item. If the pump control unit 205 determines that the user has started setting operation using the operation unit 212, the process advances from step S302 to step S303. In step S303, the pump control unit 205 transmits a start notification indicating the start of setting operation to the rack 101. Thereafter, in step S304, the pump control unit 205 waits for the end of a series of setting operations.

If the pump control unit 205 detects the end of setting operation, the process advances from step S304 to step S305. In step S305, the pump control unit 205 transmits an end notification indicating the end of operation to the rack 101. In this case, for example, the following cases can be considered as the end of setting operation:

when the user performs confirming operation for a set value (a changed set value is set in the corresponding medical pump); and when no user operation is accepted for a predetermined period of time (a set value in the process of being changed is restored to the original set value).

If the pump control unit 205 has not detected setting operation in step S302, the process advances to step S306. In step S306, the pump control unit 205 determines whether it has received an inhibition instruction from the rack 101. The issuance of an inhibition instruction and cancellation instruction from the rack 101 will be described later with reference to the flowchart of FIG. 4. Upon receiving an inhibition instruction from the rack 101, the pump control unit 205 inhibits the acceptance of setting operation from the user via the operation unit 212 in step S307. At this time, the pump control unit 205 decreases the display luminance of the display unit 202 to explicitly indicate a setting operation inhibition state. In contrast to this, if the pump control unit 205 receives a cancellation instruction from the rack 101, the process advances from step S308 to step S309. Upon inhibiting the acceptance of user operation in step S307, the pump control unit 205 cancels the inhibition state in step S309 to resume accepting setting operation by the user. If the pump control unit 205 has decreased the display luminance of the display unit 202 in step S307, the pump control unit 205 restores the display luminance of the display unit to the normal display luminance in step S309. If it is necessary to perform urgent operation at the time of, for example, the generation of a warning, the pump control unit 205 preferentially accepts operation corresponding to the warning and changes the display with respect to the above processing.

Figure 4:
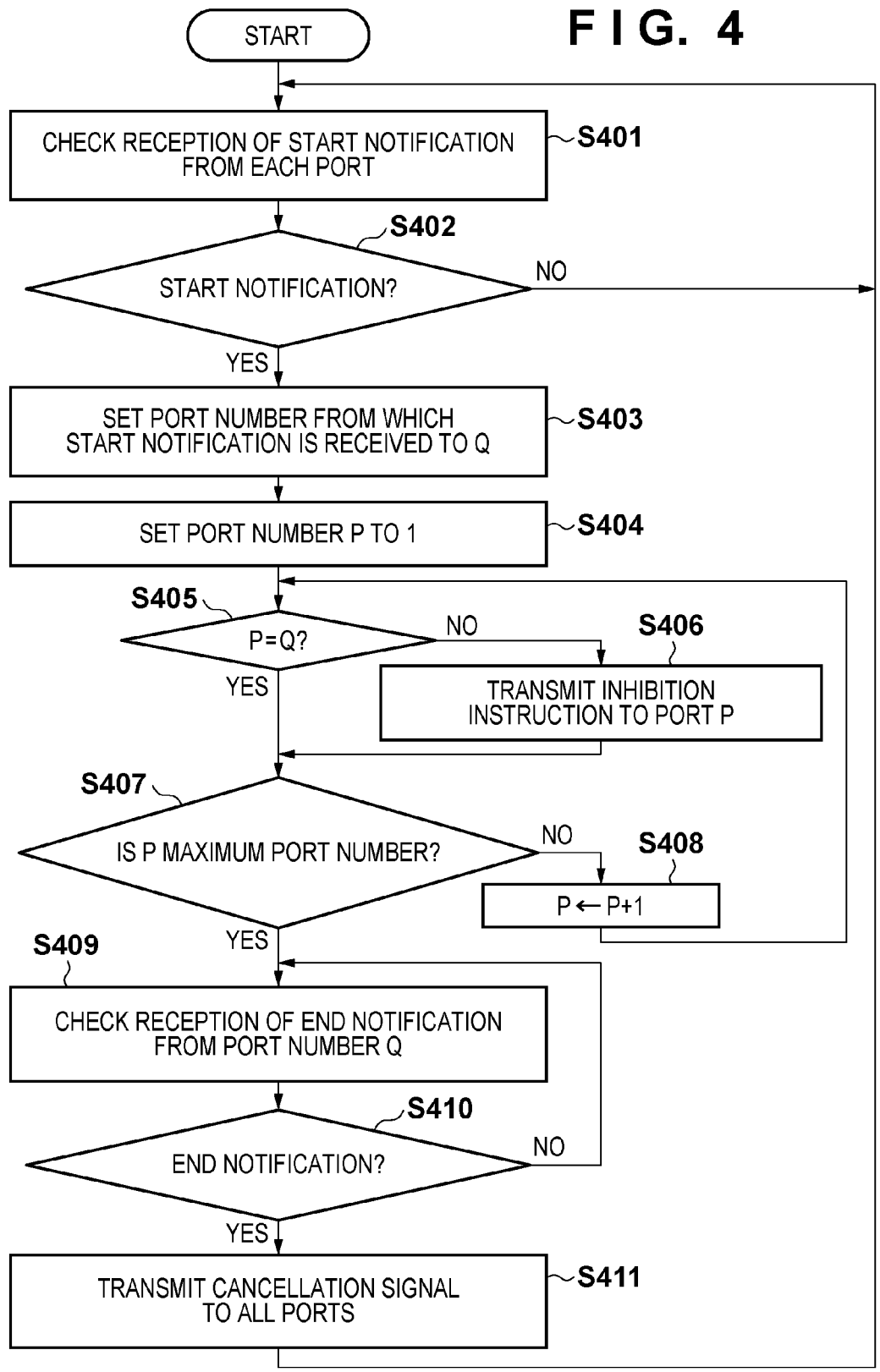
FIG. 4 is a flowchart showing a control procedure for the medical pump mounting rack according to the first embodiment.
Figure 5:
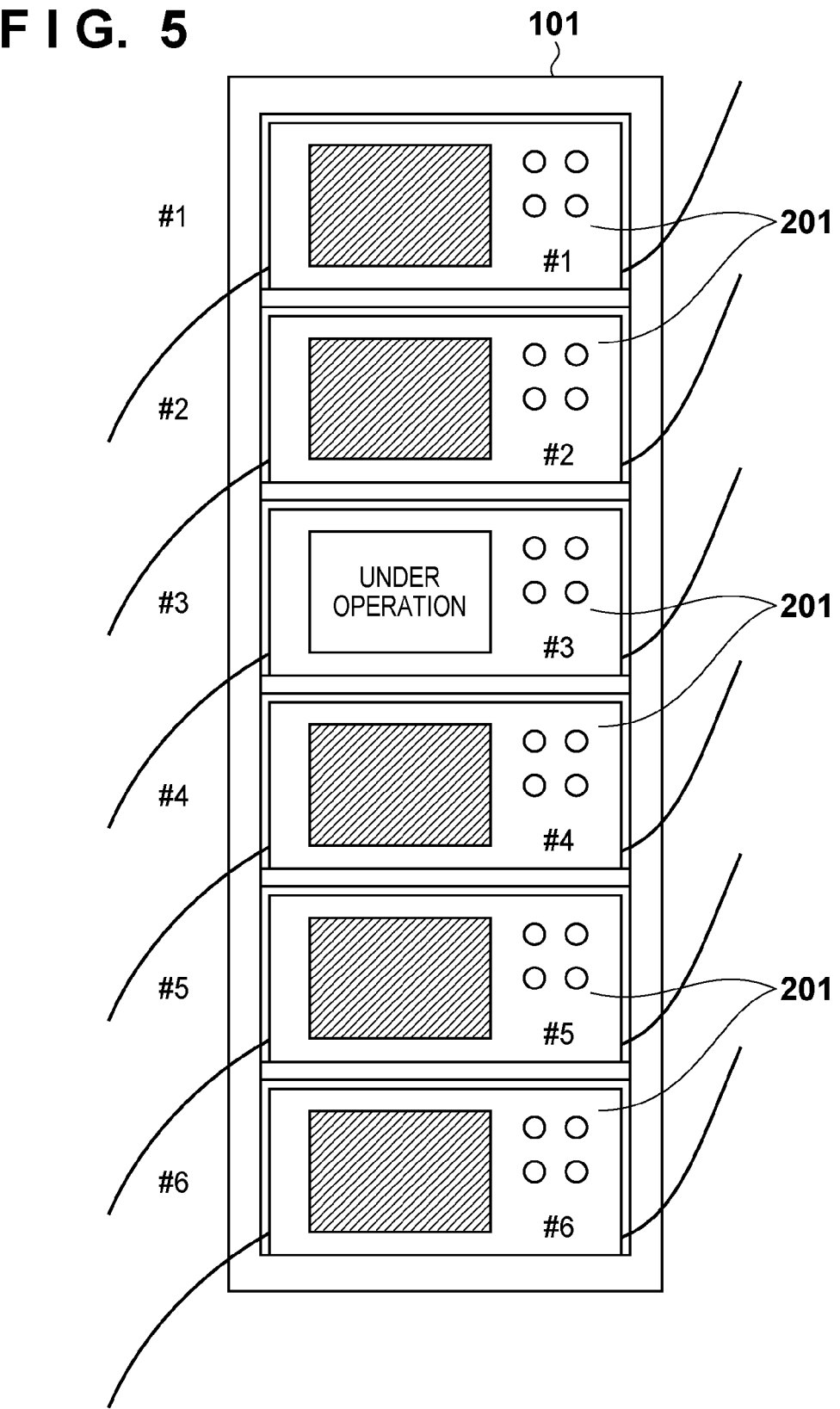
FIG. 5 is a view showing an example of operation including a medical pump under operation in the medical pump system according to the first embodiment.

Control by the rack 101 according to this embodiment will be described next. In the embodiment, upon receiving a start notification from the mounted medical pumps 201, the rack 101 transmits an inhibition instruction to inhibit the acceptance of operation on another medical pump. FIG. 4 is a flowchart for explaining processing by the rack 101 according to this embodiment. FIG. 5 is a view for explaining the display state of the medical pumps other than the medical pump of #3 while the user is performing setting operation for it. The operation of the rack 101 will be described in detail below with reference to FIGS. 4 and 5.

In step S401, the control unit 121 checks a port from which a start notification from the medical pumps 201 has been received via the communication module 111 and the ports 102 of #1 to #6. As described above, since the communication module 111 notifies the control unit 121 of a pair of a port number and a warning notification, the control unit 121 can know a specific medical pump connected to a specific one of the ports of #1 to #6 on which the user is performing setting operation. When the control unit 121 receives a start notification from one medical pump, the process advances from step S402 to step S403. If the medical pumps 201 receives no start notification, the medical pumps 201 repeats step S401.

In step S403, the control unit 121 sets the port number of the port from which the start notification has been received to a variable Q. In step S404, the control unit 121 sets "1", which is the first port number (the number of the port located at the top in this case), as the port number corresponding to a processing target, to a variable P. The control unit 121 repeats the processing in steps S405 to S418 until the variable P coincides with the maximum port number (6 in this case), thereby performing processing for all the ports (the ports of #1 to #6 in this case). In the following description, ports of port numbers P and Q are sometimes referred to as port P and port Q, respectively.

In step S405, the control unit 121 determines whether port P is the port which has received the start notification, by determining whether P=Q. If P=Q does not hold, the medical pump connected to port P is a medical pump (another medical pump) which has not transmitted the start notification. In step S406, therefore, the control unit 121 transmits an inhibition instruction to port P to inhibit setting operation on the corresponding medical pump. The process then advances to step S407. If P=Q holds, the process directly advances from step S405 to step S407. In this case, the control unit 121 transmits no inhibition instruction to the medical pump corresponding to port Q under operation.

In step S407, the control unit 121 determines whether it has performed the above processing for all the ports, by determining whether the variable P is the maximum port number (6 in this case). If the variable P is not the maximum port number, the control unit 121 increments P by one in step S408. The process then returns to step S405 to perform the processing in steps S405 to S408 for the next port. If the variable P has reached the maximum port number, it indicates that the control unit 121 has completed the transmission of an inhibition instruction to all the medical pumps except for the medical pump which has performed operation notification. The process therefore advances to step S409.

In steps S409 and S410, the control unit 121 waits for the reception of an end notification from port Q which has received the start notification. That is, in step S409, the control unit 121 checks whether it has received an end notification from the medical pump which has transmitted the start notification (the medical pump connected to port Q). If the control unit 121 has not received an end notification, the process returns from step S410 to step S409. If the control unit 121 has received an end notification, the process advances from step S410 to step S411. In step S411, the control unit 121 transmits a cancellation instruction for cancelling the operation inhibition states of the medical pumps to all the ports. Note that the control unit 121 may be configured to transmit a cancellation instruction to all the ports except for port Q.

With the above processing, according to the medical pump system of this embodiment, if there is a medical pump on which setting operation has been performed, it is possible to inhibit operation on the remaining medical pumps. This makes it possible to prevent erroneous operation on a wrong medical pump. In addition, as shown in FIG. 5, decreasing the display luminances of the display units 202 of the remaining medical pumps (#1, #2, #4, #5, and #6) allows the user to quickly recognize the medical pump under operation.

According to the above description, a medical pump which has received an inhibition instruction decreases or restores the display luminance of the display unit 202 by its own control. However, the present invention is not limited to this. For example, the rack 101 may issue an inhibition instruction and an instruction to decrease display luminance, and the corresponding medical pump may be set in an operation inhibition state and decreases the display luminance of the display unit 202 in accordance with the instruction. In this case, in step S411, the control unit 121 transmits an instruction to restore the display luminances to all the ports (or all the ports except for port Q). In order to allow the user to easily specify a medical pump under operation, the control unit 121 decreases the display luminances of medical pumps on which setting operation is inhibited. However, the present invention is not limited to this, and the display color may be changed. The above description has exemplified the arrangement including the medical pumps vertically arranged in a line as shown in FIG. 1. However, the present invention is not limited to this. For example, obviously, a medical pump system may use a rack in which medical pumps are horizontally arranged in a line or two-dimensionally arranged in a plurality of lines in the vertical and horizontal directions. In addition, the present invention may be applied to a case in which not all the medical pumps are mounted in the rack.

Second Embodiment

The second embodiment will exemplify an arrangement configured to perform display to more explicitly indicate a medical pump under operation by displaying a graphic pattern having a direction attribute (for example, an arrow) instead of or in addition to the operation of decreasing the display luminance of the display unit. The second embodiment will refer to both the arrangement 6a in which the medical pumps are vertically arranged in a line and the arrangement 6b in which the medical pumps are two-dimensionally arranged in a plurality of lines in the vertical and horizontal directions.

Figure 6:
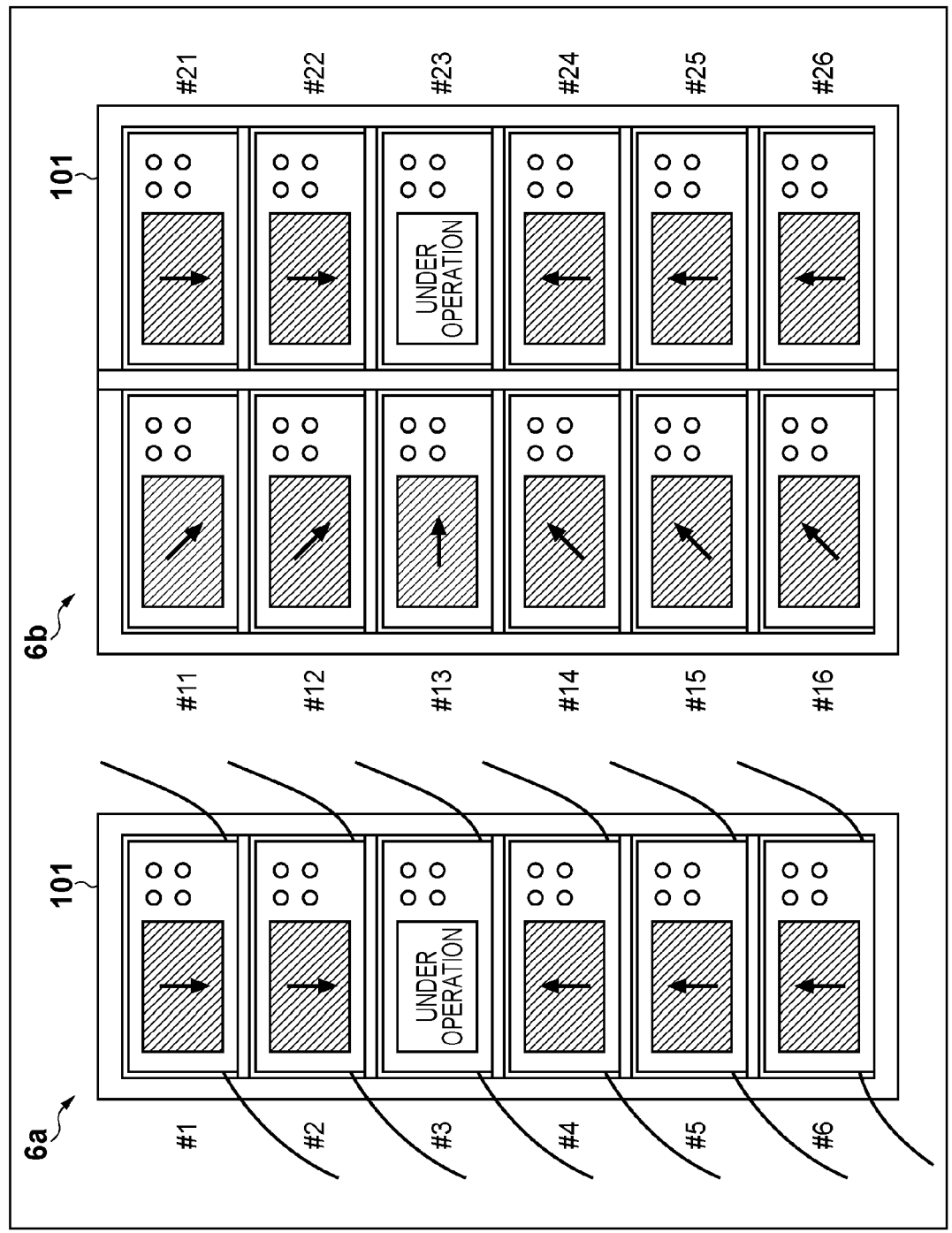
FIG. 6 is a view showing an example of operation including a medical pump under operation in the medical pump system according to the first embodiment.

If medical pumps are vertically arranged in a line as in the case of the arrangement 6a in FIG. 6, assigning port numbers in ascending order from the top can grasp the relative positional relationship between the respective port numbers. If medical pumps are arranged two-dimensionally as in the case of the arrangement 6b in FIG. 6, each port number is formed from a two-digit number, with the upper digit indicating a specific column and the lower digit indicating a specific ordinal number, in order to specify the specific column and ordinal number at which the port is located. For example, in the arrangement 6b, "1" and "2" are respectively assigned to the right and left columns, #11 to #16 are set as the six port numbers on the right column, and #21 to #26 are set as the six port numbers on the left column. This makes it possible to determine the relative, two-dimensional positional relationship between a warning port and other ports.

Figure 7:
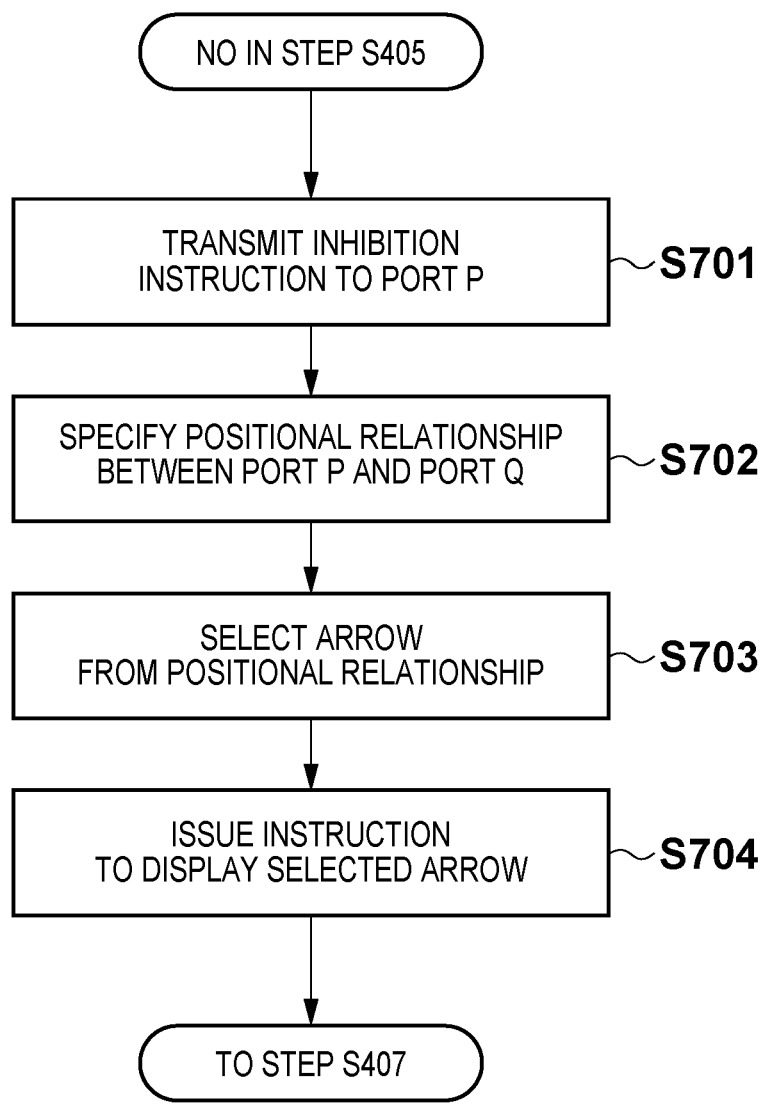
FIG. 7 is a flowchart for explaining processing for displaying the mount position of a medical pump under operation by using the display unit of the remaining medical pumps.

FIG. 7 is a flowchart for explaining control for issuing an instruction to perform arrow display in the second embodiment. A control unit 121 executes the processing shown in FIG. 7, which replaces step S406 in FIG. 4. First of all, in step S701, the control unit 121 transmits an inhibition instruction to the corresponding port (the port of number P) to inhibit setting operation on the corresponding medical pump (as in step S406).

In step S702, the control unit 121 specifies the positional relationship between target port P and port Q which has received an operation start notification in a rack 101. For example, if the rack 101 is a vertical-one-line type as in the case of the arrangement 6a in FIG. 6, and port numbers are assigned in ascending order from the top, the vertical positional relationship can be specified as follows from the magnitude relationship between P and Q:

If P<Q, port P is located above port Q. (a-1):

If P>Q, port P is located below port Q. (a-2):

Even if port numbers are assigned as in the arrangement 6b in FIG. 6, the positional relationship between port P and port Q can be specified from the following relationships:

If upper digit of P=upper digit of Q, port P is located at same column as that of port Q. (b-1):

If upper digit of P<upper digit of Q, port P is located on left side of port Q. (b-2):

If upper digit of P>upper digit of Q, port P is located on right side of port Q. (b-3):

If lower digit of P<lower digit of Q, port P is located above port Q. (b-4):

If lower digit of P>lower digit of Q, port P is located below port Q. (b-5):

If lower digit of P=lower digit of Q, port P is located right beside port Q. (b-6):

In step S703, the control unit 121 selects the direction of an arrow to be displayed on the medical pump connected to port P from the positional relationship between port P and port Q specified in step S702. If medical pumps are vertically mounted in a line in the rack 101 as in the case of the arrangement 6a in FIG. 6, the control unit 121 selects either upward arrow or downward arrow in accordance with the positional relationship between P and Q. In the arrangement 6a, the control unit 121 selects a downward arrow for port P located above port Q, and selects an upward arrow for port P located below port Q. If the rack 101 has a two-dimensional port array as in the case of the arrangement 6b in FIG. 6, the control unit 121 selects one of eight directions, namely upward, downward, leftward, rightward, and oblique directions. In the arrangement 6b, for example, since P=12 and Q=23 concerning the port of #12, (b-2) and (b-4) are satisfied. The control unit 121 therefore selects a lower right arrow concerning the port of #12.

In step S704, the control unit 121 outputs a display instruction to cause the medical pump corresponding to port P to display the arrow with the direction selected in the above manner. The medical pump decreases the luminance upon receiving the inhibition instruction transmitted in step S701, and displays the arrow in accordance with the display instruction transmitted in step S704. The above processing implements the display of the arrangements 6a and 6b shown in FIG. 6. The display unit of each medical pump which is not being operated decreases the display luminance and displays the arrow indicating the mount position of the medical pump under operation. This allows the user to quickly recognize the medical pump under operation upon seeing the rack in which the plurality of medical pumps are mounted.

The second embodiment is configured to decrease the luminance display and perform arrow display concerning each medical pump which is not being operated. However, the operation of decreasing the display luminance may be omitted. In addition, in the first and second embodiments, each medical pump decreases the luminance of the display unit upon receiving an inhibition instruction to inhibit operation. However, the present invention is not limited to this. For example, the rack 101 may transmit an inhibition instruction and a luminance decrease instruction to each medical pump to make the medical pump inhibit operation and decrease the display luminance of the display unit in accordance with the two instructions. In addition, the display control described in the second embodiment can be applied to a case in which medical pumps are arrayed in three or more lines. This makes it possible to decide an arrow to be displayed on each medical pump. Note that the arrows to be displayed is not limited to those in the eight directions described above. The rack 101 may instruct the direction of an arrow with an angle to draw and display an arrow with the instructed angle on the medical pumps 201. However, a graphic pattern to be displayed is not specifically limited as long as it indicates a direction, and is not limited to an arrow. In addition, the present invention may be applied to a case in which not all the medical pumps are mounted in the rack.

Third Embodiment

Figure 8:
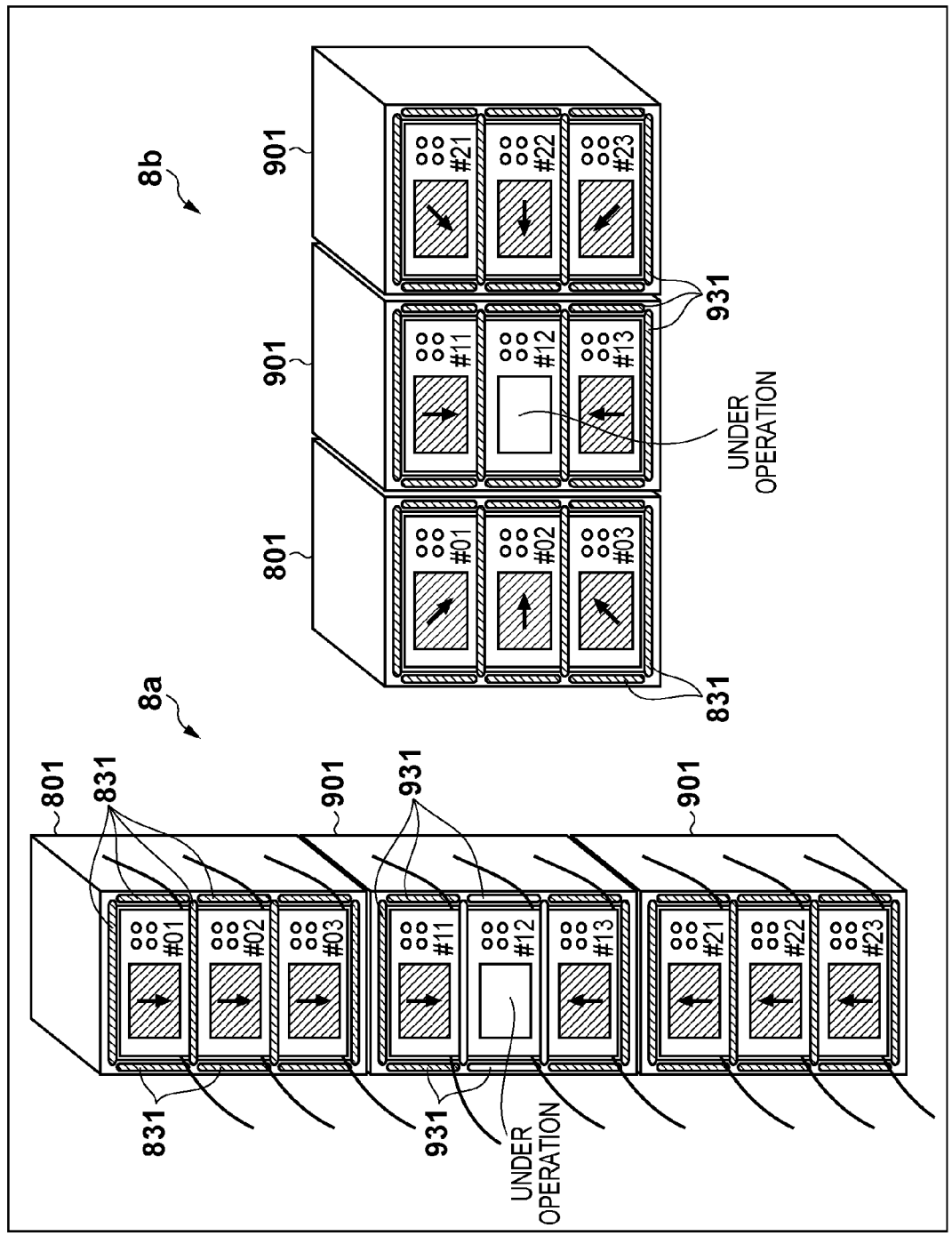
FIG. 8 is a view showing an example of the overall arrangement of a medical pump system according to the second embodiment.

The first and second embodiments have exemplified the arrangement configured to mount the plurality of medical pumps 201 in the single rack 101. The third embodiment is an embodiment configured to flexibly construct a medical pump system by coupling a plurality of racks each capable of mounting a plurality of medical pumps 201. FIG. 8 shows an example of the outer appearance of the medical pump system according to the third embodiment. In an arrangement 8*a* in FIG. 8, two subsidiary racks 901 are vertically connected to a main rack 801. In this arrangement, the medical pumps are arrayed in a line in the vertical direction. The main rack 801 and the subsidiary racks 901 each can mount three medical pumps 201. In the arrangement 8*a*, nine medical pumps are vertically arrayed in a line. In an arrangement 8*b* in FIG. 8, the main rack 801 and the two subsidiary racks 901 are horizontally arrayed, and nine medical pumps are two-dimensionally arrayed (vertically and horizontally arrayed in a 3×3 matrix). The arrangements 8*a* and 8*b* in FIG. 8 are provided with light-emitting units 831 and 931 surrounding the respective mount positions of the pumps. Selectively turning on the light-emitting units surrounding the mount position of a medical pump under operation will indicate the medical pump under operation more clearly to the user. FIG. 8 shows a state in which the light-emitting units surrounding the mount position of #12 are ON to explicitly indicate the mount position (#12) of the medical pump under operation to the user.

Figure 9:
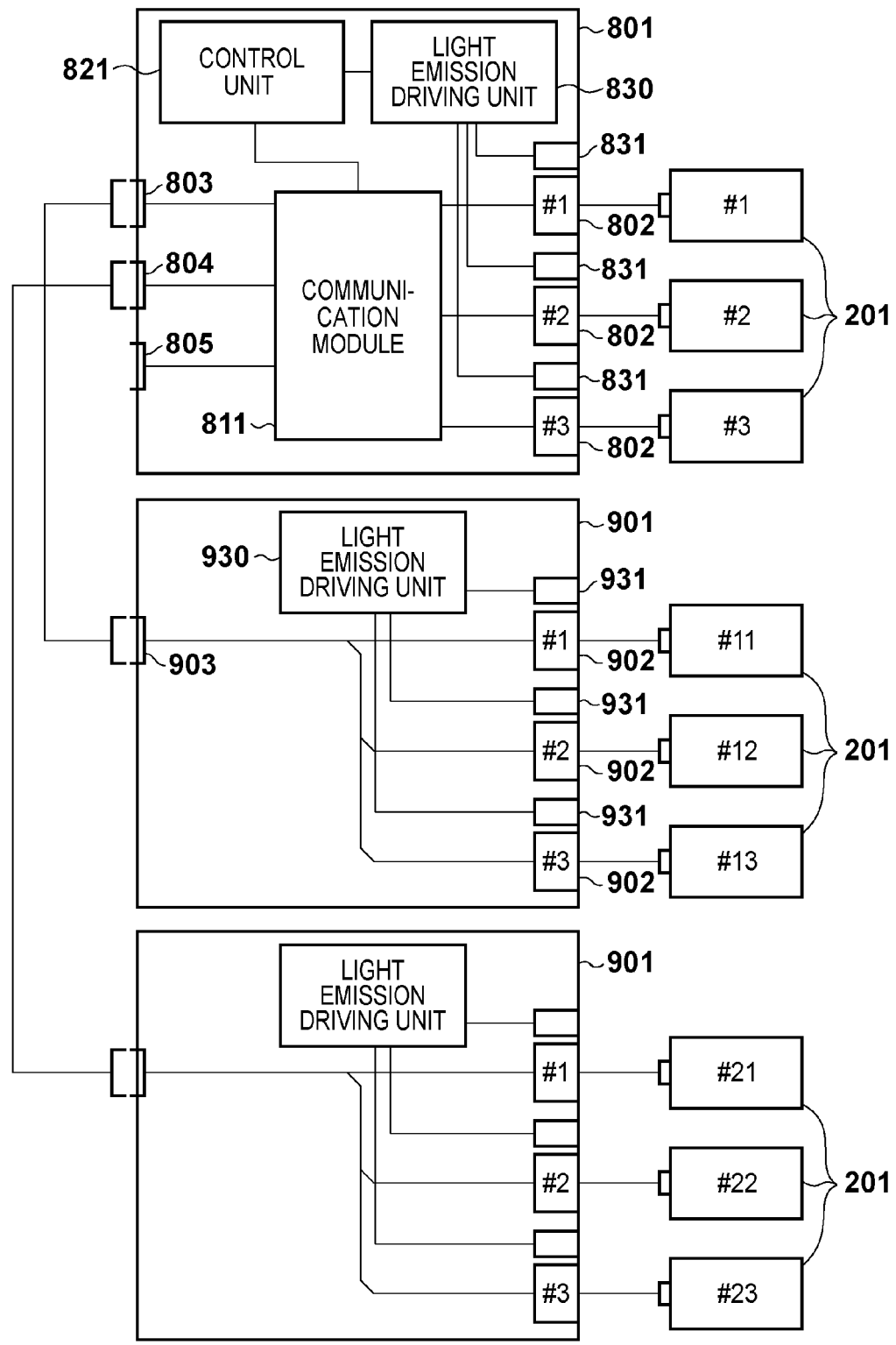
FIG. 9 is a block diagram for explaining a control arrangement for a medical pump mounting rack according to the second embodiment.

FIG. 9 is a block diagram for explaining a control function for the rack arrangements indicated by the arrangements 8*a* and 8*b* in FIG. 8. The main rack 801 includes a plurality of ports 802, a control unit 821, and a communication module 811, like the rack 101 according to the first embodiment. The main rack 801 further includes connectors 803, 804, and 805 for connecting the subsidiary racks 901. Light emission driving units 830 each selectively drive the plurality of light-emitting units 831 to explicitly indicate a specific mount position to the user in accordance with an instruction from the control unit 821.

The subsidiary rack 901 includes a plurality of ports 902 for communicative connection to medical pumps and a connector 903 for connection to one of the connectors 803 to 805 of the main rack 801. In the subsidiary rack 901, each signal line of the plurality of ports 902 is connected to the single connector 903. A light emission driving unit 930 of the subsidiary rack 901 is connected to the control unit 821 via one of the connectors 803 to 805 and the connector 903, and selectively drives the plurality of light-emitting units 931 to explicitly indicate a specific mount position to the user.

Upon receiving a signal from the subsidiary rack 901 connected to one of the connectors 803 to 805 of the main rack 801, the communication module 811 obtains a value by adding a predetermined number to the port number of the subsidiary rack 901 as a port number and provides it as a corresponding signal to the control unit 821. The predetermined number to be added is set in advance for each of the connectors 803 to 805. For example, 10, 20, and 30 are respectively set for the connectors 803, 804, and 805. When a subsidiary rack 901 is to be added, the subsidiary rack 901 located immediately below or on the right side of the main rack 801 is connected to the connector 803, and the subsidiary rack 901 located below or on the right side of the subsidiary rack is connected to the connector 804. For example, upon receiving a start notification/end notification from the port of #2 of the subsidiary rack 901 connected to the connector 803, the communication module 811 adds 10 as the predetermined number to the port number and notifies the control unit 821 of the resultant number indicating the reception of the notification from the port of #12. Likewise, upon receiving a start notification/end notification from the port of #3 of the subsidiary rack 901 connected to the connector 804, the communication module 811 adds 20 as the predetermined number to the port number set for the connector 804 and notifies the control unit 821 of the resultant number indicating the reception of the notification from the port of #23.

According to the above arrangement, the control unit 821 handles the port numbers of the medical pumps connected to the respective racks as #01, #02, . . . , #23, as indicated in the arrangements 8*a* and 8*b* in FIG. 8. This makes it possible to inhibit the operation of medical pumps other than the medical pump under operation and make the display units of the remaining medical pumps indicate the medical pump under operation by applying the processing described in the first and second embodiments. Note that in the arrangements 8*a* and 8*b*, when the medical pump corresponding to the port of #12 transmits a start notification, the remaining medical pumps decrease the display luminances of the display units and perform direction display.

In addition, in the third embodiment, the control unit 821 selectively drives the light-emitting units 831 and 931, of the light-emitting units 831 and 931, which surround the mount position (the mount position of the medical pump which has transmitted the operation start notification) corresponding to port Q. This more clearly indicates the position of the pump which is being operated by the user. The arrangements 8*a* and 8*b* in FIG. 8 each are configured to selectively drive the light-emitting units 831 and 931 surrounding the mount position of the port of #12. Note that it is also possible to explicitly indicate a medical pump under operation by using only the light-emitting units provided in a rack upon omitting display control in each display unit (decreasing the display luminance and performing arrow display like those described in the first and second embodiments).

Note that this system may be configured to allow the user to set predetermined numbers respectively assigned to the connectors 803 to 805. It is possible to implement this arrangement by, for example, providing digital switches near the connectors 803 to 805, respectively, so as to allow the user to set predetermined numbers. Alternatively, the system may be configured to set additional values for the port numbers of the main rack 801 itself. This makes it possible to change the order of the main rack 801 and the subsidiary racks 901 by setting additional values to the port numbers of the subsidiary racks 901. For example, it is possible to locate the main rack 801 at the lowermost position in the arrangement 8*a* or locate the main rack 801 in the middle column in the arrangement 8*b*.

In addition, the maximum number of pumps mounted in each rack is three. However, the present invention is not limited to this. Alternatively, the present invention can also be applied to a case in which not all medical pumps are mounted in each rack. If, however, the additional values to be assigned to the connectors 803 to 805 are 10, 20, and 30, respectively, as described above, the maximum number of pumps in each subsidiary rack is 10.

In the third embodiment, the main rack 801 and the subsidiary rack 901 including no control unit are connected to each other. However, the present invention is not limited to this. If the main rack 801 is configured to be able to switch the main/subsidiary relationship, it is possible to link a plurality of main racks 801 to each other. For example, a main/subsidiary relationship switch may be provided for the main rack 801, and the control unit 821 may control the communication module 811 such that if "main" is selected, the rack functions as a main rack, whereas if "subsidiary" is selected, the rack functions as a subsidiary rack. If the rack functions as a subsidiary rack, for example, settings are made in advance to use the connector 803 instead of the connector 903. This allows the intelligent main rack 801 to function as a main or subsidiary unit. This makes it possible to flexibly change a medical pump system.

As described above, like the first and second embodiments, the third embodiment is configured to inhibit operation on medical pumps other than a medical pump under operation to prevent operation errors. In addition, since the mount position of a medical pump under operation is explicitly indicated by the light-emitting units of the remaining medical pumps or the light-emitting units provided in the rack, the user can easily specify the medical pump under operation.

The first to third embodiments each have exemplified the state in which medical pumps are mounted at all the mount positions in the rack. Obviously, however, this system operates without any problems even if pumps are set in the rack as if some teeth are missing.

The present invention is not limited to the above embodiments and various changes and modifications can be made within the spirit and scope of the present invention. Therefore, to apprise the public of the scope of the present invention, the following claims are made.

REFERENCE SIGNS LIST

101: medical pump mounting rack, 102-107: port, 201: medical pump, 202: display unit, 111, 204: communication module, 121: control unit, 203: connector, 205: pump control unit, 206: infusion mechanism

What is claimed is:

1. A medical pump system including a plurality of medical pumps mounted in a rack, wherein
    said rack comprises
        a communication unit configure to communicate with a plurality of mounted medical pumps,
        a determination unit configured to determine whether a start notification indicating a start of setting operation or an end notification indicating an end of setting operation is received from one of said plurality of medical pumps via said communication unit,
        a first transmission unit configured to, if said determination unit determines that the start notification is received from said one medical pump, transmit an inhibition instruction to inhibit acceptance of user operation to all remaining medical pumps except for said one medical pump via said communication unit, and
        a second transmission unit configured to, if said determination unit determines that the end notification is received from said one medical pump, transmit a cancellation instruction to cancel the inhibition state set by the inhibition instruction to all said remaining medical pumps, and
    each of said plurality of medical pumps comprises a control unit configured to inhibit acceptance of user operation during an interval between reception of the inhibition instruction and reception of the cancellation instruction.

2. The medical pump system according to claim 1, wherein said first transmission unit transmits a display instruction to decrease display luminance of a display unit of a medical pump when transmitting the inhibition instruction, and
    said second transmission unit transmits a display instruction to restore the display luminance of said display unit when transmitting the cancellation instruction.

3. The medical pump system according to claim 1, further comprising
    a specifying unit configured to specify a mount position of said one medical pump, in said rack, which has transmitted the start notification, and
    a decision unit configured to decide direction display to cause said remaining medical pumps to perform display to indicate the mount position specified by said specifying unit from each of said remaining medical pumps other than said medical pump which has transmitted the start notification,
    wherein said first transmission unit transmits a display instruction to cause a display unit of a medical pump to perform direction display decided by said decision unit, when transmitting the inhibition instruction.

4. The medical pump system according to claim 1, wherein said control unit of said medical pump changes a display state of a display unit of said medical pump in accordance with the display instruction.

5. The medical pump system according to claim 1, wherein said control unit of said medical pump decreases display luminance of a display unit of said medical pump while inhibiting acceptance of user operation based on the inhibition instruction.

6. The medical pump system according to claim 1, wherein said rack further comprises
    light-emitting units provided in correspondence with a plurality of mount positions at which medical pumps are to be mounted, and
    a driving unit configured to selectively drive said light-emitting units so as to explicitly indicate a position at which said one medical pump is mounted in an interval after determining by said determination unit that the start notification is received until determining by said determination unit that the end notification is received.

7. A medical pump mounting rack configured to mount a plurality of medical pumps, comprising:
    a communication unit configured to communicate with a plurality of mounted medical pumps;
    a determination unit configured to determine whether a start notification indicating a start of setting operation or an end notification indicating an end of setting operation is received from one of said plurality of medical pumps via said communication unit;
    a first transmission unit configured to, if said determination unit determines that the start notification is received from said one medical pump, transmit an inhibition instruction to inhibit acceptance of user operation to all remaining medical pumps except for said one medical pump via said communication unit; and
    a second transmission unit configured to, if said determination unit determines that the end notification is received from said one medical pump, transmitting a cancellation instruction to cancel the inhibition state set by the inhibition instruction to all said remaining medical pumps.

* * * * *